United States Patent [19]

Duke

[11] Patent Number: 5,142,900

[45] Date of Patent: Sep. 1, 1992

[54] APPARATUS AND METHOD FOR TESTING VISCOSITY

[76] Inventor: Horace W. Duke, 8371 Highway 49, Pleasant View, Tenn. 37146

[21] Appl. No.: 599,057

[22] Filed: Oct. 17, 1990

[51] Int. Cl.$^5$ .................................................. G01N 11/10
[52] U.S. Cl. .................................................... 73/54.39
[58] Field of Search ............................... 73/59, 60, 54

[56] References Cited

U.S. PATENT DOCUMENTS

| | | | |
|---|---|---|---|
| 2,707,391 | 5/1955 | McSkimin | 73/59 |
| 4,155,250 | 5/1979 | Dürner | 73/60 |
| 4,570,478 | 2/1986 | Soong | 73/60 |
| 4,893,500 | 1/1990 | Fink-Jenson | 73/60 |

Primary Examiner—Hezron E. Williams
Assistant Examiner—Michael Brock
Attorney, Agent, or Firm—James C. Kesterson

[57] ABSTRACT

Apparatus and method for determining the viscosity of printer ink is disclosed. The apparatus includes a vertically mounted rod supported by a base. A strain gauge or load cell measures strain or pulling force existing between the base and the rod. A collar having a diameter slightly greater than the diameter of the rod and suitable for receiving a sample of ink at the gap between the rod and the collar is moved at a precise velocity. The viscosity of the ink sample is then calculated from the known physical parameters of the apparatus, the rate of shear, temperature, and the shear stress or pulling load exerted on the rod by the movement of the collar and ink sample as they travel along the length of the rod.

16 Claims, 2 Drawing Sheets

APPARATUS AND METHOD FOR TESTING VISCOSITY

TECHNICAL FIELD

This invention relates to Apparatus and Methods for determining the viscosity of liquid, and more specifically to a highly accurate computer controlled apparatus and method for determining the viscosity of printing ink.

BACKGROUND ART

As will be appreciated by those skilled in the printing industry, it is very important to precisely monitor and control certain of the rheological characteristics of printing inks. More specifically, and because the flow rate of printing inks is extremely complex, it is important to be able to measure properties such as viscosity. As is further understood by those skilled in the art, viscosity is defined as the ratio of shear stress "S" to shear rate "D". Shear stress "S" equals the shearing force, and shear rate "D" is the velocity gradient through the stressed liquid.

At the present time, perhaps the best known technique for determining the viscosity of printing ink is the "Falling Rod Viscometer". In fact, "The American Society For Testing And Materials" located in Philadelphia, Pa. has included a standard test for measuring the viscosity of printing inks by means of "falling rod type equipment" in its *ANNUAL BOOK OF ASTM STANDARDS*. The test is entitled "Standard Test Method for Viscosity of Printing Inks and Vehicles by the Falling-Rod Viscometer" and has a designation of: D 4040-89, and is incorporated herein in its entirety by reference. Typical of the equipment used for such testing is the LARAY Viscometer manufactured by the LHOMARGY Co. of Draviel, France; "Thwing-Albert Model LR" maufactured by Thwing-Albert Instrument Co., 10960 Dutton Road, Philadelphia, Pa.; and "Churchill" manufactured by Churchill Instrument Co., Ltd., Greenford, England. As the name of the test indicates, and as well known by those skilled in the printing industry, the presently available apparatus includes a stationary collar through which a rod (having a diameter only slightly less than the inside diameter of collar) is allowed to free fall. A sample of material to be tested is introduced to the small clearance between the rod and the collar such that the viscosity of the printing ink or other material being tested determines how fast the length of the rod travels through the collar due to gravity. For higher viscosity materials additional weights can be added to the top of the falling rod to increase the speed at which it falls through the collar. Thus, from the above, it will be appreciated that those factors necessary for determining viscosity can be measured and/or determined. Namely, the applied force due to the weight of the falling rod, the unit area based on the diameter of the rod and depth of the collar, and of course the velocity at which the rod falls.

Reasonably acceptable results can be obtained from this type of equipment when measuring materials of fairly high viscosity. However, unacceptable errors often occur when the equipment is used to measure materials having a viscosity below or in the range of about 10 poise. The reason for the unacceptable results is because the weight of the filling rod even without additional weights is simply so great that the rod falls too fast to obtain reliable results.

Therefore, it is an object of this invention to provide highly accurate apparatus and method to determine the viscosity of printing inks.

It is another object of this invention to provide substantially automatic apparatus and method for determining the viscosity of printing ink.

It is yet another object of the present invention to provide apparatus and method for measuring low viscosity materials below about 10 poise.

SUMMARY OF THE INVENTION

Other objects and advantages will be obvious, and will in part appear hereinafter, and will be accomplished by the present invention which provides apparatus and method for determining the viscosity of a liquid material such as printing ink. The apparatus includes a base which supports an elongated rod having a first and further end, and a selected length and diameter. The rod is typically supported in a vertical orientation and is surrounded by a collar which has an inside diameter only slightly greater than the diameter of the rod. The clearance between the collar and the rod is on the order of about 0.0035 cm and 0.0055 cm, and is preferably 0.0045 cm. A sample of the printing ink or other material to be tested is introduced into the clearance such that movement of the collar along the rod is resisted by the viscosity of the material under test. A drive means is coupled to move the collar at a selected speed between a position proximate the first end of the rod to a position proximate the further end. A strain gauge load cell or other means connected between the base and rod measures the force or strain between the base and rod due to the pulling force imposed on the rod by the viscosity of the material filling the clearance between the rod and the collar as the collar moves along the length of the rod. In a preferred embodiment, a second drive means rotates the rod prior to the test to assure even distribution of the test sample completely around the rod and collar at the clearance. The preferred embodiment further includes a means for measuring the temperature of the sample as well as a computer to compute the viscosity of the test sample. If the temperature is not within a preset range, the test will be interrupted until the temperature of the sample is in the proper range.

BRIEF DESCRIPTION OF THE DRAWINGS

The above mentioned features of the invention will be more clearly understood from consideration of the following description in connection with the accompanying drawings in which.

BEST KNOWN MODE FOR CARRYING OUT THE INVENTION

Figure 1:
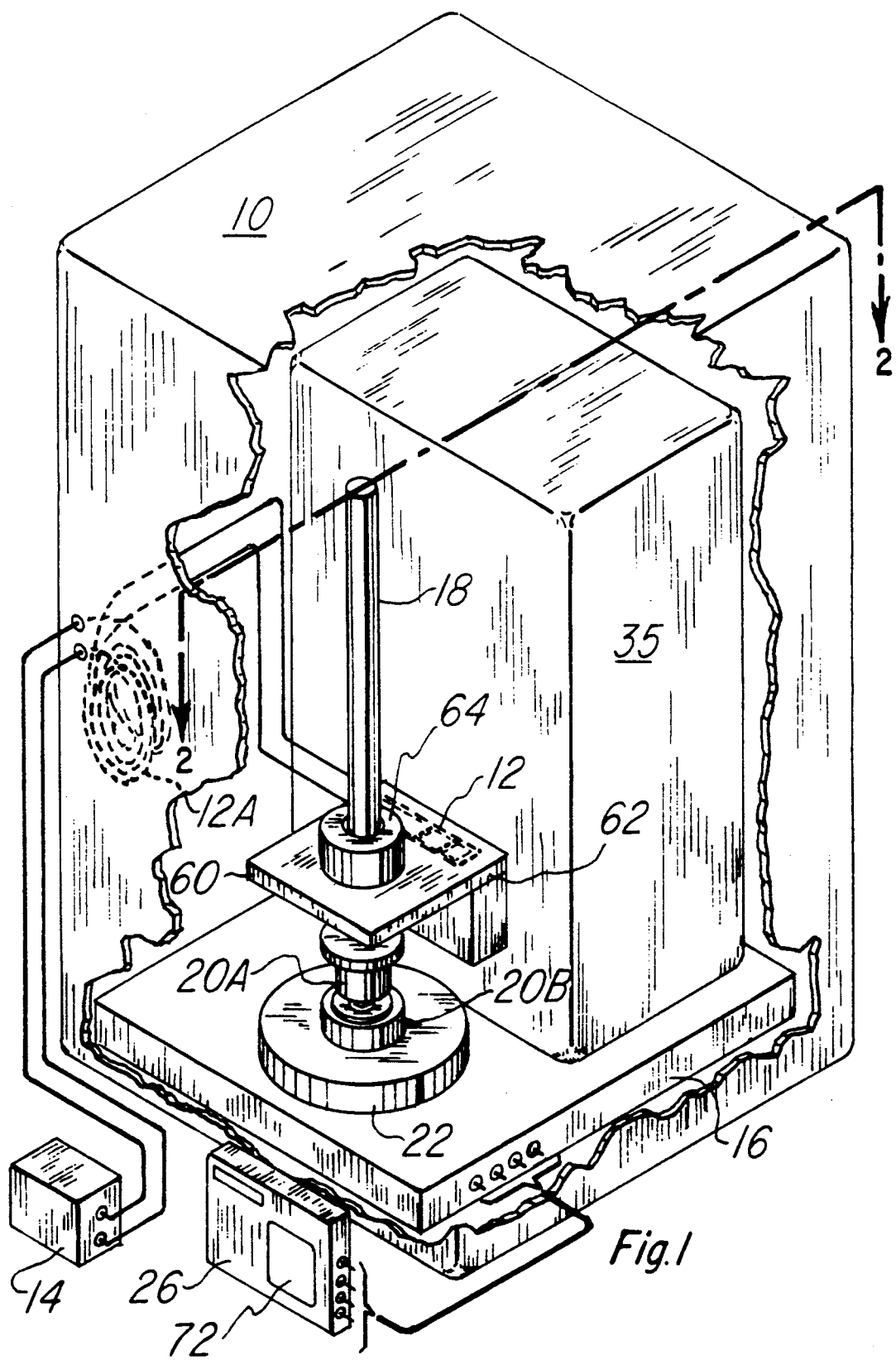
FIG. 1 is a perspective view of a preferred embodiment of the apparatus of this invention.
Figure 2:
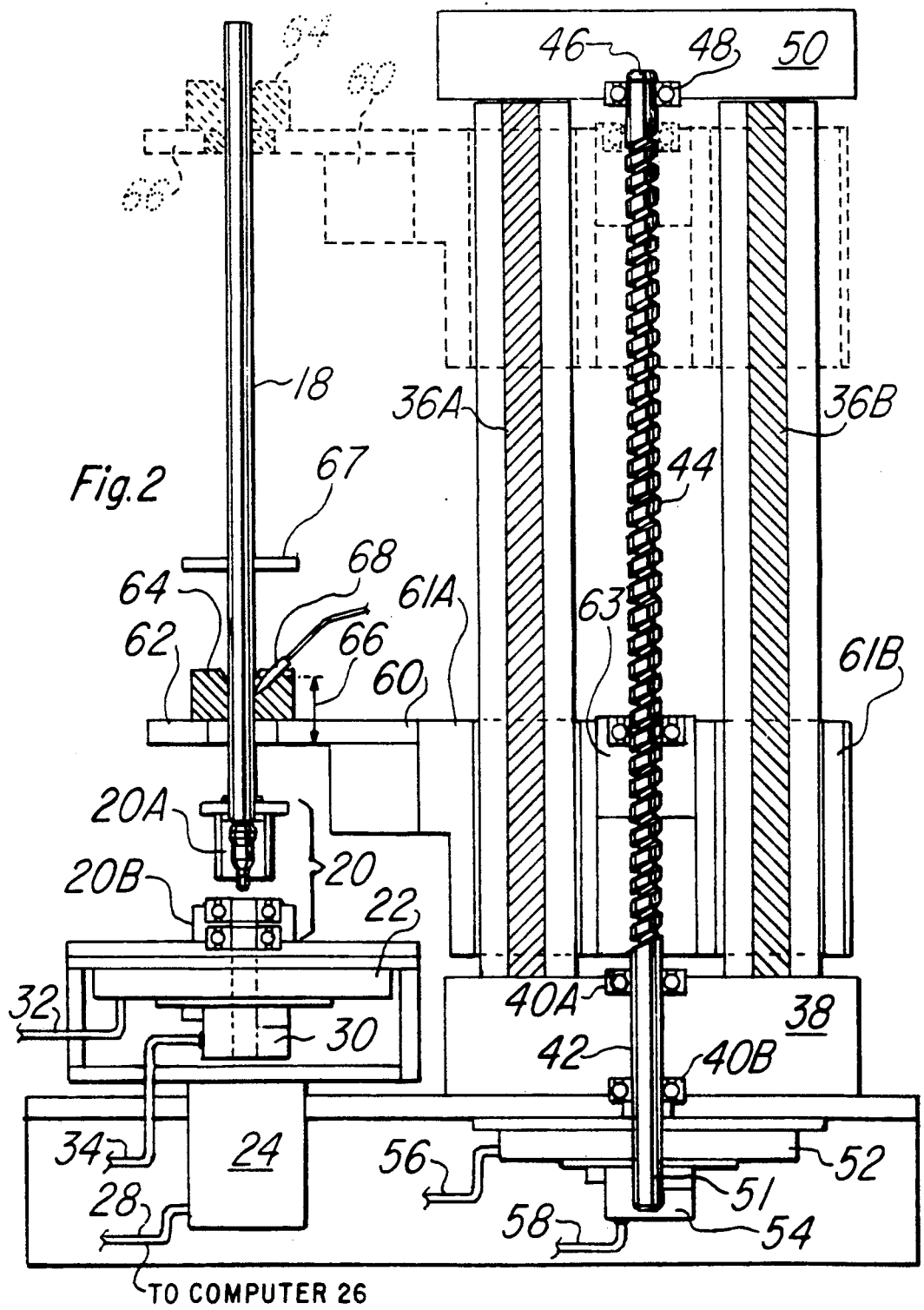
FIG. 2 is section view taken along lines 2—2 of FIG. 1.

Referring now to the FIG., there is shown a preferred embodiment of the present invention. As shown, the invention includes an enclosure 10 for precisely controlling and maintaining a desired temperature within the enclosure. Although not essential to be used with the apparatus, if the temperature should be maintained between plus or minus one degree centigrade, a temperature control system such as a water bath having cooling channels 12 machined into moving carriage 60 to be discussed hereinafter. Alternately other apparatus for temperature control may be used. As an example, coils 12A are shown cooling the entire enclosure. A heating/cooling source 14 is shown connected to channels 12 and/or coils 12A. Within enclosure 10 there is included a base 16 supporting a vertical rod 18. Vertical rod 18 is connected to base 16 through a two part quick disconnect coupling 20A and 20B and a drive means 22. The first part 20A of the two part quick disconnect is a part of, or is secured to rod 18, while the second part of the quick disconnect is mounted to drive means 22. Thus, it will be appreciated that by incorporating a part 20A of the quick disconnect to a selection of rods 18 having different diameters or made of different materials, various different types of rods may be readily selected. In the preferred embodiment of the present invention, a rod diameter of about 1.2 cm has been found particularly suitable. Drive means 22 is suitable for rotating and providing a limited amount of axially movement to rod 18. Also included is a means for measuring the force or strain between base 16 and rod 18, such as a strain gauge or load cell 24. Load cell 24 provides an electrical signal representative of any strain between base 16 and rod 18 to a control means such as computer 26 by means of line 28. In the preferred embodiment an ultra precision strain gauge load cell having a capacity of between 0.0 grams to about a maximum of about 12 K-grams, and preferably about 9.5 K-grams has been found to be particularly suitable. In the preferred embodiment, drive means 22 is a servo motor which works in cooperation with encoder 30. Both the servo motor 22 and encoder 30 are also mounted and controlled by computer 26 via lines 32 and 34 respectively.

Also mounted to and supported by base 16 is a carriage system designated generally by reference number 35. The carriage system includes a pair of elongated slide rails 36A and 36B mounted vertically to bearing block 38 such that both rails 36A and 36B extend parallel to rod 18. Bearing block 38 is secured to base 16 and includes two sets of aligned bearings 40A and 40B for rotationally supporting the bottom portion 42 of an elongated ball screw 44 which is also aligned parallel to rod 18. When required, the top end 46 of elongated ball screw 44 may be rotationally supported by another bearing 48 mounted on a top support member 50 which is itself supported by the top portions of vertical slide rails 36A and 36B. The bottom end 50 of ball screw 44 is connected to a second rotational drive means such as servo motor 52 and an encoder 54. It will be appreciated, of course, that types of motors other than servo motors would also be suitable so long as they can supply a smooth constant force to ball screw 44, and can rotate ball screw 44 at different selected speeds. In the illustrated embodiment, the rotational speed of ball screw 44 is precisely controlled by servo motor 52 in cooperation with encoder 54 by means of computer 26 through lines 56 and 58 respectively.

A carriage 60 includes two sets of linear bearings 61A and 61B which travel along slide rails 36A and 36B. A zero-backlash preloaded ballnut 63 which travels along ball screw 44 is also mounted to carriage 60. Thus, rotation of the ball screw 44 by servo motor 52 results in movement of carriage 60 along slide rails 36A and 36B. Encoder 54 is selected to have a position accuracy of about 0.00004 inches, and the rotational speed of servo motor 52 is selected so as to provide a linear travel speed of between about 0.0025 inches per second and 10 inches per second. This range of speeds would equate to drop times of about 0.4 seconds and 1,600 second of the prior art falling rod viscometer. It will be appreciated by those skilled in the art that the of encoders with servo motors, such as encoders 30 and 54 provides the capability to precisely log in data, monitor carriage 60 for proper movement, end to adjust acceleration, rate of travel and distance of travel.

In the preferred embodiment, the over all length of slide rails 36A and 36B and the number of rotations of servo motor 52 are selected to provide a total travel distance of the carriage of about nine inches. Also mounted to carriage 60 ia a support extension 62 for supporting collar 64. Collar 64 has an inside diameter which is only slightly greater than the diameter of rod 18. Assuming a diameter of 1.2 cm for rod 18, a collar bore having a mean gap clearance of between about 0.0035 cm and 0.0055 cm with a preferred gap of 0.0045 cm has been found to be particularly suitable. The depth of the collar 64 represented by double headed arrow 66 is preferably selected to provide a total "shearing" area of about 10.5 sq cm with a gap of 0.0045. In the preferred embodiment of the invention, urethane wipers 67 are provided to close about rod 18 to assist in spreading the test sample as will be discussed further hereinafter. The preferred embodiment further includes a low mass precision temperature sensor 68 mounted in collar 64 and having a response time of less than one second with a sensitivity of 0.01 degrees centigrade for monitoring the temperature of the sample under test. As shown, temperature sensor 68 also provides its output to computer 26. As will be discussed hereinafter the monitored temperature may indicate that the test should be interrupted until the temperature of the sample under the test reaches a predetermined range.

As has been discussed, both servo motors 22 and 52 and encoders 30 and 54 along with the output of load cell 24 and temperature sensor 68 are all connected to and/or controlled by computer 26. According to one embodiment, a controller or a computer 26 which has been found to be suitable includes a 80286 processor running at 12 MHz, and which samples the inputs from load cell 24, temperature sensor 68 and the collar position (encoder 58) at a rate of 12,500 samples per second with a resolution accuracy of 16 bits. Of course, a faster or larger computer could be used to obtain even more exact results. Form these sampled inputs and the data relevant to the physical parameters of the apparatus such as travel distance, the velocity of the carriage as it moves along rod 18, the total "shearing area", and the gap between rod 18 and collar 64 it will be appreciated that viscosity of the sample under test can be readily computed. Other parameters that may be computed include shear stress, shear rate, yield stress, apparent viscosity @ 2500 sec, and the degree of non-Newtonianism. It will further be appreciated that various of the computed or monitored parameters may be displayed as graphs on screen 72 or computer 26. In addition, the computer may be programmed to provide step by step instructions to an operator of the equipment.

The testing of a sample of printing ink could typically proceed as follows. After first turning the system on, the operator will be prompted by an instruction step appearing on display screen 72 to load an existing test sequence by identifying name or I.D. number, or to create a test sequence by using built in test generation menus. The operator then opens the enclosure, secures a rod 18 having a selected diameter and a selected surface via quick disconnect 22A and 22B and puts the ink sample onto the rod immediately above collar 64. The operator then closes the enclosure. The computer will then ascertain that the enclosure doors were actually opened and closed, that a rod is in place, and that the temperature is within a proper range, etc. Once the enclosure 10 is closed, and the computer has verified the test setup, rod 18 is coated with the ink sample by controlling servo motors 22 and 52 so as to move the collar up about ¾ of an inch while slowly rotating the rod. This process ensures uniform dispersal of the ink sample around the rod 18 and collar 64. The apparatus is then operated so as to precoat rod 18 by activating servo motor 52 and moving the collar upwards to spread the test sample uniformly across the surface of the rod. Urethane wipers 67 then close around rod 18 as servo motor 52 moves collar 64 down toward the bottom of the rod again to further spread the test sample across the surface of rod 18. After the rod is precoated, the temperature of the sample is measured by temperature sensor 68. If the temperature is within a predetermined range, the test will continue. If not, the test is delayed until the proper temperature range is achieved. Once the temperature of the test sample is within the predetermined limits, servo motor 52 then moves collar 64 from a bottommost starting point with a precise and preselected velocity to top point. During the travel time, the strain on the strain gauge load cell and the temperature of the sample under test is sampled 12,500 times per second. Once the movement of collar 64 is complete, the shear rate and shear stress is computed and the carriage is returned to the bottommost position.

To assure accuracy of the test results, it will be appreciated that a programmed test sequence may require the collar to move up and down the rod several times at the same or different rates of travel.

It is further noted that the prior art falling rod type viscometer required the elongated rod to be carefully oriented in a vertical position prior to being allowed to free fall. However, it is believed that since the servo motor 52 precisely controls the relative speed between rod 18 and collar 64, and precisely measures the strain between the rod and its support resulting from the pulling or shearing force of the test sample on the rod, that the apparatus of the present invention will provide acceptable results even if rod 18 was mounted at some angle, including horizontally.

Thus although there have been described herein particular embodiments of the apparatus and method for determining the viscosity of liquid materials such as printers ink, it is not intended that such specific references be considered as limitations upon the scope of this invention except in so far as is set forth in the following claims.

I claim:

1. Apparatus for determining the viscosity of a liquid sample comprising:
  a base;
  an elongated rod having a first and further end, and a selected diameter and length supported by said base;
  means for sensing strain occurring between said base and said rod;
  a collar surrounding said rod, said collar having an inside diameter slightly greater than said rod, and said collar and said rod suitable for receiving a liquid to be tested in the slightly greater space between said rod and said collar;
  a drive means coupled to said collar for moving said collar a selected speed along said rod;
  a second drive means for achieving rotation between said rod and said collar, said second drive means operable to distribute said sample around the circumference of said rod before said apparatus determines the viscosity of said liquid sample;
  an enclosure with at least said elongated rod and said collar located therein; and
  a temperature control system for maintaining the interior of said enclosure at a selected temperature.

2. The apparatus of claim 1, wherein said sensing means provides an electrical signal representative of said strain between said rod and said base, and further comprising means connected to said sensing means for receiving said electrical signal and monitoring said strain between said base and said rod.

3. The apparatus of claim 2 wherein said sensing means is a strain gauge.

4. The apparatus of claim 1 wherein said rod is oriented in a vertical position with said first end at a lowermost point and said collar coupled to said drive means to move said collar from a location proximate said first end of said rod toward said further end.

5. The apparatus of claim 1 and further comprising means for monitoring the temperature of the liquid being tested.

6. The apparatus of claim 1 and further comprising a control means connected to said drive means, said means controlling said drive means to move said collar between said first and second positions along said rod.

7. The apparatus of claim 6 wherein said sensing means provides an electrical signal representative of said strain and wherein said control means receives said electrical signal and computes the viscosity of said liquid.

8. The apparatus of claim 7 wherein said means for monitoring temperature provides an electrical representation of said temperature to said control means.

9. Apparatus for measuring the viscosity of a sample of printing ink comprising:
  a base;
  an elongated rod having a first and further end, and a selected diameter and length, said first said first end of said rod mounted to said base and said rod vertically oriented with said first end down;
  means for sensing strain occurring between said base and said elongated rod and for providing an electrical signal representative of said strain;
  a collar surrounding said rod, said collar having an inside diameter such that a clearance of between about 0.0035 cm and 0.0055 cm exists between said rod and said rod, and said collar and said rod suitable for receiving a sample of ink at said clearance between said rod and said collar;
  a carriage support means mounted to said base;
  a carriage coupled to said collar and suitable for moving along said carriage support means;
  a first drive means for moving said carriage such that said collar moves between a first position proximate said first position of said and a second position said further end of said rod;
  a second drive means for rotating said rod, said second drive means operable to distribute said sample of printing ink around the circumference of said rod;
  a computer for causing said second drive means to distribute said ink around the circumference of said rod before controlling said drive means such that said collar moves at a selected speed between said first and second positions, said computer further receiving said electrical signal from said sensing means and computing the viscosity of said sample of ink;

an enclosure with at least said elongated rod and said collar located therein; and a temperature control system for maintaining the interior of said enclosure at a selected temperature.

10. The apparatus of claim 9 and further comprising means for monitoring the temperature of the liquid being tested.

11. The apparatus of claim 10 wherein said means for monitoring temperature provides an electrical representation of said temperature to said control means.

12. An automated method for determining the viscosity of a liquid comprising the steps of:

providing an elongated rod vertically mounted to a base;

surrounding said elongated rod with a collar having an inside diameter slightly greater than the diameter of said rod;

placing a sample of liquid to be tested in the space between said collar and said elongated rod and on the top side of said collar;

rotating said rod to distribute said liquid sample around said rod, and then;

moving said collar at a selected speed from a first position proximate the bottom of said rod to a second position proximate the top of said rod;

measuring the strain between said base and said rod as said collar with said liquid moves between said first position to said second position.

13. The method of claim 12 and further comprising the steps of monitoring the temperature of said liquid sample and interrupting said moving step until said temperature achieves a preselected temperature.

14. Apparatus for determining the viscosity of a liquid sample comprising:

a base;

an elongated rod having a first and further end, and a selected diameter and length supported by said base;

means for sensing strain occurring between said base and said rod;

a collar surrounding said rod, said collar having an inside diameter slightly greater than said rod, and said collar and said rod suitable for receiving a liquid to be tested in the slightly greater space between said rod and said collar;

a first drive means coupled to said collar for moving said collar between said first and further ends at a selected speed along said rod; and a second drive means for achieving rotation of said rod with respect to said collar operable to distribute said sample around said rod before said apparatus determines the viscosity of said liquid sample.

15. Apparatus for determining the viscosity of a liquid comprising:

a base;

an elongated rod having lower and upper portions, and a selected diameter and length supported by said base;

means for sensing strain occurring between said base and said rod;

a collar surrounding said rod, said collar having an inside diameter slightly greater than said rod, and said collar and said rod suitable for receiving a liquid to be tested in the slightly greater space between said rod and said collar; and a first drive means coupled to said collar for moving said collar at a selected speed along said rod from said lower portion to said upper portion;

a second drive means for achieving rotation of said rod with respect to said collar operable to distribute said sample around said rod before said apparatus determines the viscosity of said liquid sample.

16. The method of claim 12 and further including the step of moving said collar along said rod about ¾ of an inch during said rotation.

* * * * *